United States Patent

Bonse et al.

[11] 4,328,340
[45] May 4, 1982

[54] PREPARATION OF 4-AMINO-6-TERT.-BUTYL-3-ALKYLTHIO-1,2,4-TRIAZIN-5-(4H)-ONES

[75] Inventors: Gerhard Bonse, Cologne; Heinz U. Blank, Odenthal; Hans Krätzer, Wuppertal, all of Fed. Rep. of Germany

[73] Assignee: Bayer Aktiengesellschaft, Leverkusen, Fed. Rep. of Germany

[21] Appl. No.: 235,496

[22] Filed: Feb. 19, 1981

[30] Foreign Application Priority Data

Mar. 8, 1980 [DE] Fed. Rep. of Germany ....... 3009043

[51] Int. Cl.³ ............................................ C07D 253/06
[52] U.S. Cl. .................................................... 544/182
[58] Field of Search .......................................... 544/182

[56] References Cited

U.S. PATENT DOCUMENTS 4,175,188 11/1979 Klenk et al. ..................... 544/182

FOREIGN PATENT DOCUMENTS 2732797 8/1979 Fed. Rep. of Germany.

Primary Examiner—John M. Ford
Attorney, Agent, or Firm—Sprung, Felfe, Horn, Lynch & Kramer

[57] ABSTRACT

In the preparation of 4-amino-6-tert.-butyl-3-methylthio-1,2,4-triazin-5-(4H)-one of the formula

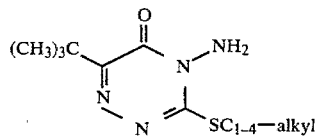

wherein pivaloyl cyanide of the formula (CH₃)₃C—CO—CN is reacted to form an intermediate, the intermediate is condensed with thiocarbohydrazide of the formula

NH₂—NH—CS—NH—NH₂ to form 4-amino-6-tert.-butyl-3-mercapto-1,2,4-triazin-5-(4H)-one of the formula

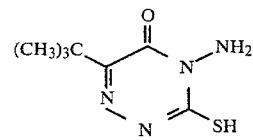

and the 4-amino-6-tert.-butyl-3-mercapto-1,2,4-triazin-5-(4H)-one is alkylated to replace the H atom on the sulphur by —C₁₋₄—alkyl, the improvement which comprises reacting the pivaloyl cyanide with a carboxylic acid anhydride of the formula

R—CO—O—CO—R in which R is an optionally substituted aliphatic radical with up to 8 carbon atoms or an optionally substituted phenyl radical, in the presence of a strong acid at a temperature between about −50° and +150° C., and then directly reacting the reaction mixture thus obtained with the thiocarbahydrazide. Advantageously R is CH₃, the strong acid is concentrated sulphuric acid, the pivaloyl cyanide is effected at a temperature between about 0° and 100° C., the condensation with thiocarbohydrazide is effected, in the presence of a mineral acid, in an aqueous or aqueous-alcoholic medium, and the alkylation is effected using methyl iodide or methyl bromide in the presence of sodium hydroxide at about 0° to 50° C.

20 Claims, No Drawings

PREPARATION OF 4-AMINO-6-TERT.-BUTYL-3-ALKYLTHIO-1,2,4-TRIAZIN-5-(4H)-ONES

The present invention relates to an unobvious process for the preparation of 4-amino-6-tert.-butyl-3-alkylthio-1,2,4-triazin-5(4H)-ones, which are known as a herbicides.

Processes for the preparation of 4-amino-6-teri.-butyl-3-methylthio-1,2,4-triazin-5(4H)-one (I) starting from pivaloyl cyanide or other pivalic acid derivatives have already been disclosed. They differ in the method of the preparation of the intermediate product 4-amino-6-tert.-butyl-3-mercapto-1,2,4-triazin-5(4H)-one (V).

According to DE-OS (German Published Specification) No. 2,165,554, the triazinone (I) can be prepared by reacting pivaloyl chloride with an isonitrile, hydrolyzing the imidechloride formed to give the corresponding trimethylpyruvic acid amide, reacting the amide further with thiocarbohydrazide and methylating the resulting cyclization product (V) (yields: 60–82% of theory of (V); 49–67% of (I), in each case relative to pivaloyl chloride).

According to DE-OS (German Published Specification) No. 2,221,771, it is possible to prepare the said triazinone (I) by a process in which a pivalic acid amide, for example pivalanilide, is converted into the corresponding pivalimidochloride by chlorination, for example by means of thionyl chloride, this product is reacted with a metal cyanide, for example copper(I) cyanide, or hydrogen cyanide, if appropriate in the presence of a catalyst, to give the corresponding α-iminonitrile, the latter is cyclized by reaction with thiocarbohydrazide to give 4-amino-6-tert.-butyl-5-imino-3-mercapto-1,2,4-triazine, the 5-imino group is then hydrolyzed to the 5-keto group, whereupon the intermediate product (V) is obtained, and this product is subsequently methylated (yields: 42–57% of theory of (V); 35–47% of theory of (I), in each case relative to pivalanilide).

Both processes require an exceptional degree of technical effort and proceed with unsatisfactory yields and are thus unsuitable for application on a large industrial scale.

According to U.S. Pat. No. 4,175,180 the said triazinone (I) can be prepared by reacting pivaloyl cyanide with t-butanol or isobutylene in a so-called Ritter reaction to give trimethylpyruvic acid N-t-butylamide and cyclizing this product, if necessary after prior hydrolysis to the free trimethylpyruvic acid, with thiocarbohydrazide to give the intermediate product (V) and then methylating the latter (yields: 51–67% of theory of (V); 41–54% of (I), in each case relative to pivaloyl cyanide).

The process last mentioned has the fundamental disadvantage that the trimethylpyruvic acid N-t-butylamide obtained as an intermediate product can be further reacted only with relative difficulty; this applies both to the hydrolysis to the free keto-acid and to the cyclization reaction with thiocarbohydrazide.

Acid hydrolysis of trimethylpyruvic acid N-t-butylamide to give trimethylpyruvic acid is thus effected, in a yield of only 75% of theory, by heating under reflux in 5 N HCl for 10 hours and subsequent extractive working up with $CH_2Cl_2$, dilute aqueous NaOH solution, concentrated hydrochloric acid and ethyl acetate.

If prior hydrolysis of the α-keto-carboxylic acid N-t-butylamide is dispensed with and this compound is reacted directly with thiocarbohydrazide, the cyclization product 4-amino-6-t-butyl-3-mercapto-1,2,4-triazin-5(4H)-one can be isolated in yields of only 72% of theory after heating the mixture under reflux for several hours (up to 8 hours).

Moreover, experiments have shown the reaction of α-keto-carboxylic acid N-alkylamides with thiocarbohydrazide according to DE-OS (German Published Specification) No. 2,165,554 and U.S. Pat. No. 4,175,188 does not proceed to give 4-amino-6-t-butyl-3-mercapto-1,2,4-triazin-5(4H)-one as a single product, but proceeds with the formation of numerous by-products.

The present invention now provides a process for the preparation of 4-amino-6-tert.-butyl-3-methylthio-1,2,4-triazin-5(4H)-one of the formula

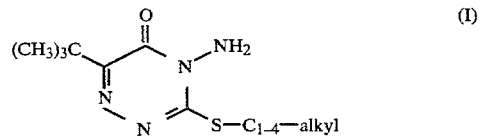

in which, in a first stage, pivaloyl cyanide of the formula $$(CH_3)_3C-CO-CN \qquad (II)$$

is reacted with a carboxylic acid anhydride of the general formula $$R\text{-}CO\text{-}C\text{-}CO\text{-}R \qquad (III),$$

in which R represents an optionally substituted aliphatic radical with up to 8 carbon atoms or an optionally substituted phenyl radical, in the presence of a strong acid and if appropriate in the presence of a solvent, at a temperature between about −50° and +150° C., the reaction mixture thus obtained is then reacted directly with thiocarbohydrazide of the formula $$NH_2-NH-CS-NH-NH_2 \qquad (IV),$$

and the 4-amino-6-tert.-butyl-3-mercapto-1,2,4-triazin-5(4H)-one formed in this reaction, of the formula

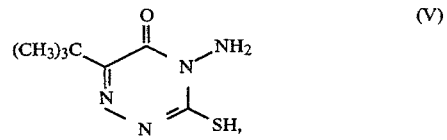

is separated off and, in a second stage, this intermediate product (V) is alkylated (which can be effected in the customary manner).

By means of the present invention, the compound (I) can be obtained, starting from pivaloyl cyanide, in a high yield and in high purity in a surprisingly simple manner.

Compared with the state of the art, the first stage of the process according to the invention is an absolutely novel and advantageous procedure in which it is possible, for the first time, for pivaloyl cyanide to be converted directly, in a surprisingly smooth and uniform reaction, into exceptionally pure 4-amino-6-tert.-butyl-3-mercapto-1,2,4-triazin-5(4H)-one (V) in almost quantitative yield under mild conditions in a "one-pot process", without any intermediate products having to be isolated.

The process according to the invention avoids the abovementioned disadvantages associated with the comparable processes for the preparation of the herbicidal active compound (I) which are already known; this means a very considerable technical simplification.

Compared with other processes, which are already known (see, for example, DE-OS'en (German Published Specifications) Nos. 2,003,144, 2,460,889, 2,460,909 and 2,648,300), for the preparation of the active compound (I) from other pivalic acid derivatives or pinacoline, the process according to the invention likewise has the industrial advantage of being highly simplified. Compared with the processes starting from pinacoline, the different raw material basis is to be regarded as an additional advantage.

If, in the first process stage, acetic anhydride is used as the carboxylic acid anhydride of the general formula (III) and concentrated sulphuric acid is used as the strong acid and, in the second stage, methyl bromide is used as the alkylating agent, the course of the reaction in the process according to the invention can be illustrated by the following equation:

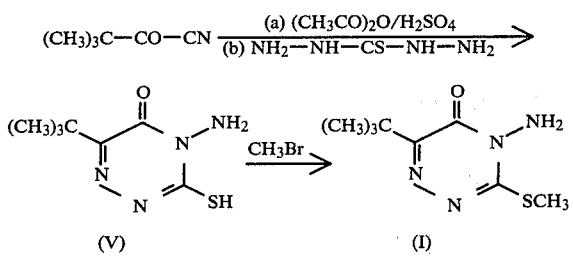

The pivaloyl cyanide (II) used as the starting material is known and can be prepared, for example, by reacting pivaloyl chloride with copper(I), cyanide (see, for example, J. Amer. Chem. Soc. 72, page 2793 (1950)).

Formula (III) provides a general definition of the carboxylic acid anhydrides also to be employed as starting substances. In this formula, R preferably represents optionally chlorine-substituted alkyl with 1 to 4 carbon atoms or phenyl.

The carboxylic acid anhydrides of the formula (III) are in some cases available on a large industrial scale, or they can be prepared by generally known methods, for example from the corresponding carboxylic acids.

Carboxylic acid anhydrides which are particularly preferred in the context of this invention are acetic anhydride, propionic anhydride and the anhydrides of chloroacetic acids.

In detail, the following statements may further be made regarding stage 1 of the process according to the invention:

The first stage of the process is carried out in the presence of a strong acid. Possible acids of this type are inorganic oxyacids, such as concentrated sulphuric acid, perchloric acid, nitric acid and phosphoric acid, and also Lewis acids, such as boron trifluoride, aluminum chloride or zinc chloride. Aliphatic and aromatic sulphonic acids and phosphonic acids and halogenoalkanecarboxylic acids, for example trichloroacetic acid, are also suitable. It is also possible to carry out the reaction in the presence of several such acids. An oxyacid, especially concentrated sulphuric acid, is preferably used.

The reaction temperatures can be varied within a substantial range in this stage of the process. In general, the reaction is carried out, as indicated above, at temperatures between −50° and +150° C., preferably between about 0° and 100° C.

The reaction is in general carried out under normal pressure.

The reaction in stage 1 of the process can be carried out in the absence or in the presence of a solvent or solubilizing agent. Possible solubilizing agents are certain organic solvents; particularly suitable solvents are glacial acetic acid and methylene chloride, and also dialkyl ethers, such as diethyl ether or diisopropyl ether, and diaryl ethers, for example diphenyl ether.

In carrying out the first stage of the process according to the invention, 0.5 to 6 mols, preferably 0.8 to 4 mols, of carboxylic acid anhydride of the formula (III) are in general employed per mol of pivaloyl cyanide of formula (II); a molar ratio of pivaloyl cyanide (II) to carboxylic acid anhydride (III) of 1:1 to 1:2 is particularly preferred.

The acids required for carrying out the first stage of the process according to the invention are employed in catalytic amounts to amounts which are greater than the stoichiometric amount. In general, 0.5 to 10 mols, preferably 0.8 to 8 mols and particularly preferably 1 to 4 mols, of acid are employed per mol of pivaloyl cyanide (II). A molar ratio of carboxylic acid anhydride (III) to strong acid of 1:2 is particularly advantageous.

Furthermore, it is particularly appropriate to employ the pivaloyl cyanide (II) and the thiocarbohydrazide (IV) in equimolar amounts.

This means that, in carrying out stage 1 of the process, it is particularly favorable to react the pivaloyl cyanide (II), the carboxylic acid anhydride (III), the strong acid and the thiocarbohydrazide (IV) in a molar ratio of 1:1:2:1 to 1:2:4:1.

If the process is carried out on an industrial scale, however, it may be advantageous to employ an excess of carboxylic acid anhydride (III) and strong acid, the molar ratio of these two components being maintained constant at 1:2, in order to keep the resulting reaction mixture readily stirrable.

It is expedient for the procedure in carrying out the first stage of the process according to the invention to be as follows:

The strong acid or a mixture of solvent and strong acid is initially introduced into the reaction vessel and the carboxylic acid anhydride (III) and the pivaloyl cyanide (II) are added successively; the reaction mixture thus obtained is introduced, either immediately after the pivaloyl cyanide has been added or after a certain subsequent stirring time (of at most 3 hours), into an aqueous or aqueous-alcoholic solution, which preferably contains mineral acid, or into an aqueous suspension of thiocarbohydrazide (IV). However, it is also possible to follow the converse procedure and to introduce the thiocarbohydrazide solution or suspension into the abovementioned reaction mixture.

The reaction times are in general 1 to 10 hours. The reaction product from the first stage of the process as a rule precipitates as crystals and can be isolated in the customary manner by filtration or by extraction.

Extraction agents which are suitable here are solvents which are not miscible with water in all proportions, for example ethers, such as diethyl ether or diisopropyl ether; esters, for example ethyl acetate; ketones, for example methyl isobutyl ketone; halogenated hydrocarbons, for example methylene chloride, chlorobenzene or dichlorobenzene; and aromatics, for example benzene, toluene, o-xylene, ethylbenzene, cumene or nitrobenzene. Methylene chloride is preferably used.

The intermediate product (V) can also exist in the form of the tautomeric 4-amino-6-tert.-butyl-5-oxo-3-thioxo-tetrahydro-1,2,4(2H,4H)-triazine of the formula

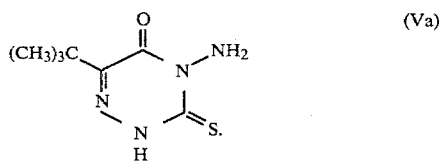

For simplicity, however, the term "4-amino-6-tert.-butyl-3-mercapto-1,2,4-triazin-5(4H)-one (V)" is always used for both tautomers (V) and (Va) in this Application.

The second stage of the process according to the invention is carried out in a known manner, by reacting (V) with, for example, a methyl halide, such as methyl bromide or methyl iodide, in the presence of a base, such as sodium hydroxide, in aqueous solution at temperatures between 0° and 50° C.

The 4-amino-6-tert.-butyl-3-methylthio-1,2,4-triazin-5(4H)-one of the formula (I) (Metribuzin) which can be prepared according to the invention is distinguished, as is known, by an outstanding herbicidal activity.

The active compound prepared according to the invention influences plant growth and can therefore be used as a defoliant, desiccant, agent for destroying broad-leaved plants, germination inhibitor and, especially, as a weedkiller. By "weeds" in the broadest sense there are meant plants growing in places where they are not desired.

Whether the compound prepared according to the invention acts as total herbicide or selective herbicide depends essentially on the amount used.

The active compound prepared according to the present invention may be used, for example, to combat the following plants:

Dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Rorippa, Rotala, Lindernia, Lamium, Veronica, Abutilon, Emex, Datura, Viola, Galeopsis, Papaver, Centaurea and Solanum; and Monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

The active compound prepared according to the present invention may be used, for example, as a selective herbicide in the following cultures:

Dicotyledon cultures of the genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita; and Monocotyledon cultures of the genera Oryza, Zea, Triticum, Hordeum, Avena, Secale, Sorghum, Panicum, Saccharum, Ananas, Asparagus and Allium.

However, the use of the active compound is in no way restricted to these genera but also embraces other plants, in the same way.

Depending on the concentration, the compound can be used for the total combating of weeds, for example on industrial terrain and railway tracks and on paths and squares with or without trees. Equally, the compound can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cacao plantations, soft fruit plantings and hopfields, and for the selective combating of weeds in annual cultures.

For combating weeds, the active compound can be used, as such or as a formulation, in admixture with other herbicides, it being possible to use finished formulations or tank mixing.

The active compound can be converted into the customary formulations, such as solutions, emulsions, suspensions, powders, foams, granules, natural and synthetic materials impregnated with active compound, and very fine capsules in polymeric substances.

These formulations may be produced in known manner, for example by mixing the active compound with extenders, that is to say liquid or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compound can be present in the formulations as a mixture with other active compounds, such as fungicides insecticides, acaricides, nematicides, bird repellents, growth factors, plant nutrients and agents which improve soil structure.

The active compound can be used as such, in the form of its formulations or in the use forms prepared therefrom by further dilution, such as ready-to-use solutions, suspensions, emulsions, powders and granules. They may be used in the customary manner, for example by watering, spraying, atomizing or scattering.

The active compound prepared according to the invention can be applied either before or after emergence of the plants. It can also be incorporated into the soil before sowing.

The amount of active compound used can vary within a substantial range. It depends essentially on the nature of the desired effect. In general, the amounts used are between 0.05 and 10 kg of active compound per hectare, preferably between 0.1 and 5 kg/ha.

The present invention also provides a herbicidal composition containing as active ingredient the compound prepared according to the present invention in admixture with a solid diluent or carrier or in admixture with a liquid diluent or carrier containing a surface-active agent.

The present invention also provides a method of combating weeds which comprises applying to the weeds, or to a habitat thereof, the compound prepared according to the present invention alone or in the form of a composition containing as active ingredient the compound in admixture with a diluent or carrier.

The present invention further provides crops protected from damage by weeds by being grown in areas in which immediately prior to and/or during the time of the growing the compound prepared according to the present invention was applied alone or in admixture with a diluent or carrier.

The preparative examples which follow are intended to illustrate the process according to the invention in more detail.

EXAMPLE 1

(A) Stage 1

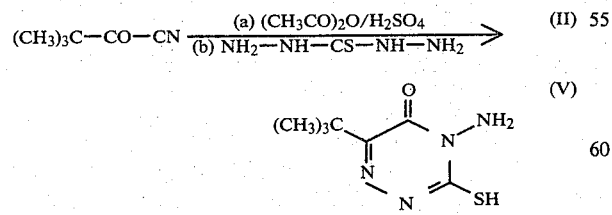

First 25.6 g (0.25 mol) of acetic anhydride and then 27.8 g (0.25 mol) of pivaloyl cyanide were introduced, in each case at room temperature, into 49.0 g (0.5 mol) of concentrated sulphuric acid, which had been initially introduced into the reaction vessel. After subsequently stirring this reaction mixture for 0.5 hour, it was stirred into a solution of 26.6 g (0.25 mol) of thiocarbohydrazide in 300 ml of 1 N HCl at 20°–30° C. When the addition had ended, the mixture was subsequently stirred at 50°–55° C. for a further 1.5 hours; after cooling, the reaction product which had precipitated was filtered off, washed with 200 ml of water and dried. 48.6 g (97% of theory) of 4-amino-6-tert.-butyl-3-mercapto-1,2,4-triazin-5(4H)-one (V) were obtained as colorless crystals of melting point 212°–214° C.; content according to a determination by gas chromatography >99%. No further purification operations were necessary for subsequent reactions.

(B) Stage 2

Methylation (V)→ (I)

48.6 g (0.243 mol) of 4-amino-6-tert.-butyl-3-mercapto-1,2,4-triazin-5(4H)-one (V) were introduced into a mixture of 236 g of 45% strength sodium hydroxide solution and 160 g of water, while stirring. When all of the product had dissolved, 40.2 g of methyl iodide were added in a manner such that the internal temperature did not exceed 30° C. When the addition had ended, the reaction mixture was stirred at room temperature for a further 2 hours. The reaction product which had precipitated was then filtered off, washed with 100 ml of water and dried. 42.5 g (82% of theory) of 4-amino-6-tert.-butyl-3-methylthio-1,2,4-triazin-5(4H)-one (I) of melting point 123°–125° C. were obtained.

EXAMPLE 2

(A) The procedure followed was as described in Example 1 A but, instead of acetic anhydride, the equivalent amount (0.25 mol) of propionic anhydride was employed. 42.0 g (84% of theory) of 4-amino-6-tert.-butyl-3-mercapto-1,2,4-triazin-5(4H)-one (V) were obtained.

(B) Methylation to give (I) was carried out according to Example 1 B.

EXAMPLE 3

(A) The procedure followed was as described in Example 1 A, but the reaction mixture of concentrated sulphuric acid, acetic anhydride and pivaloyl cyanide was introduced into an aqueous suspension of 26.6 g (0.25 mol) of thiocarbohydrazide and 300 ml of water. 45.1 g (90.1% of theory) of 4-amino-6-tert.-butyl-3-mercapto-1,2,4-triazin-5(4H)-one (V) of melting point 212°–214° C. were obtained; content, according to the gas chromatogram, >99%.

(B) The methylation to give (I) was carried out according to Example 1 B.

EXAMPLE 4

(A) stage 1

(II)→ (V)
[semi-industrial scale]

First 5.12 kg (50 mols) of acetic anhydride and then 2.78 kg (25 mols) of pivaloyl cyanide were introduced, in each case at room temperature, into 9.81 kg (100 mols) of concentrated sulphuric acid which had been initially introduced into the reaction vessel. After subsequently stirring this reaction mixture for 2 hours, it was stirred into a solution of 2.66 kg (25 mols) of thiocarbohydrazide in 30 liters of 1 N HCl at 20°–30° C. When the addition had ended, the mixture was subsequently stirred for a further 2 hours at 50°–55° C.; after cooling, the reaction product which had precipitated was filtered off, washed with 20 liters of water and dried. 4.80 kg (96% of theory) of 4-amino-6-tert.-butyl-3-mercapto-1,2,4-triazin-5(4H)-one (V) were obtained as colorless crystals of melting point 212°–214° C.; content, according to determination by gas chromatography, >99%.

The excess of acetic anhydride/concentrated $H_2SO_4$ employed compared with Example 1, the molar ratio of acetic anhydride to concentrated $H_2SO_4$ being kept constant at 1:2, served to ensure that the reaction mixture remained readily stirrable throughout the entire reaction period in the case of such a relatively large batch; the yields achieved were virtually the same in both cases.

(B) The methylation to (I) could be carried out as described in Example 1 B. However, various improved processes are also available for carrying out the methylation according to stage 2 on a large industrial scale (see, for example, DE-OS (German Published Specification) No. 2,729,761 and also U.S. Pat. Nos. 3,890,317, 3,897,429, 3,905,973 and 4,035,364).

It will be appreciated that the instant specification and examples are set forth by way of illustration and not limitation, and that various modifications and changes may be made without departing from the spirit and scope of the present invention.

We claim:

1. In the preparation of 4-amino-6-tert.-butyl-3-alkylthio-1,2,4-triazin-5-(4H)-one of the formula

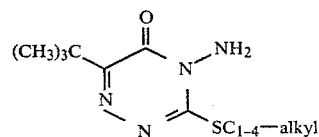

wherein pivaloyl cyanide of the formula

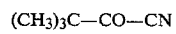

is reacted to form an intermediate, the intermediate is condensed with thiocarbohydrazide of the formula

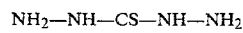

to form 4-amino-6-tert.-butyl-3-mercapto-1,2,4-triazin-5(4H)-one of the formula

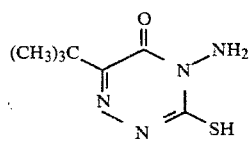

and the 4-amino-6-tert.-butyl-3mercapto-1,2,4-triazin-5(4H)-one is alkylated to replace the H atom on the sulphur by $—C_{1-4}—$ alkyl, the improvement which comprises reacting the pivaloyl cyanide with a carboxylic acid anhydride of the formula

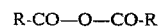

in which R is an optionally substituted aliphatic radical with up to 8 carbon atoms or an optionally substituted phenyl radical, in the presence of a strong acid at a temperature between about −50° and +150° C., and then directly reacting the reaction mixture thus obtained with the thiocarbahydrazide.

2. A process according to claim 1, wherein the reaction of the pivaloyl cyanide is effected at a temperature between about 0° and 100° C.

3. A process according to claim 1, wherein the molar ratio of the pivaloyl cyanide:carboxylic acid anhydride is about 1:0.5–10.

4. A process according to claim 1, wherein the molar ratio of the pivaloyl cyanide:carboxylic acid anhydride is about 1:0.8–4.

5. A process according to claim 1, wherein the molar ratio of the pivaloyl cyanide:carboxylic acid anhydride is about 1:1–2.

6. A process according to claim 1, wherein molar ratio of the pivaloyl cyanide:strong acid is about 1:0.5–10.

7. A process according to claim 1, wherein molar ratio of the pivaloyl cyanide:strong acid is about 1:0.8–8.

8. A process according to claim 1, wherein molar ratio of the pivaloyl cyanide:strong acid is about 1:1–4.

9. A process according to claim 1, wherein the molar ratio of the carboxylic acid anhydride:strong acid is about 1:2.

10. A process according to claim 1, wherein the molar ratio of pivaloyl cyanide:carboxylic acid anhydride:strong acid:thiocarbohydrazide is about 1:1:2:1 to 1:2:4:1.

11. A process according to claim 1, wherein R is optionally chlorine-substituted alkyl with 1–4 carbon atoms or phenyl.

12. A process according to claim 1, wherein R is $CH_3$.

13. A process according to claim 1, wherein the strong acid is an oxyacid.

14. A process according to claim 1, wherein the strong acid is concentrated sulphuric acid.

15. A process according to claim 1, wherein glacial acetic acid, methylene chloride, a diaryl ether or a dialkyl ether is employed as a solvent in the reaction with pivaloyl cyanide.

16. A process according to claim 1, wherein the reaction with pivaloyl cyanide is carried out in the absence of a solvent.

17. A process according to claim 1, wherein the condensation with thiocarbohydrazide is effected, in the presence of a mineral acid, in an aqueous or aqueous-alcoholic medium.

18. A process according to claim 1, wherein the alkylation is effected using methyl iodide or methyl bromide in the presence of a base and at about 0° to 50° C.

19. A process according to claim 18, wherein the base is sodium hydroxide.

20. A process according to claim 10, wherein R is $CH_3$, the strong acid is concentrated sulphuric acid, the reaction of the pivaloyl cyanide is effected at a temperature between about 0° and 100° C., the condensation with thiocarbohydrazide is effected, in the presence of a mineral acid, in an aqueous or aqueous-alcoholic medium, and the alkylation is effected using methyl iodide or methyl bromide in the presence of sodium hydroxide at about 0° to 50° C.

* * * * *